United States Patent
Weichert et al.

(10) Patent No.: US 10,004,818 B2
(45) Date of Patent: *Jun. 26, 2018

(54) ETHER AND ALKYL PHOSPHOLIPID COMPOUNDS FOR TREATING CANCER AND IMAGING AND DETECTION OF CANCER

(71) Applicant: CELLECTAR, INC., Madison, WI (US)

(72) Inventors: Jamey P. Weichert, Fitchburg, WI (US); Anatoly Pinchuk, Madison, WI (US); Irawati Kandela, Madison, WI (US); Marc Longino, Verona, WI (US); William R. Clarke, Colgate, WI (US)

(73) Assignee: CELLECTAR, Inc., Madison, WI (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/099,977

(22) Filed: Apr. 15, 2016

(65) Prior Publication Data

US 2016/0228588 A1 Aug. 11, 2016

Related U.S. Application Data

(63) Continuation of application No. 13/887,981, filed on May 6, 2013, now Pat. No. 9,339,564, which is a continuation of application No. 12/813,992, filed on Jun. 11, 2010, now abandoned.

(60) Provisional application No. 61/186,600, filed on Jun. 12, 2009.

(51) Int. Cl.
*A61K 51/04* (2006.01)
*A61K 45/06* (2006.01)
*C07B 59/00* (2006.01)
*A61K 31/661* (2006.01)

(52) U.S. Cl.
CPC ........ *A61K 51/0489* (2013.01); *A61K 31/661* (2013.01); *A61K 45/06* (2013.01); *A61K 51/0408* (2013.01); *C07B 59/00* (2013.01)

(58) Field of Classification Search
CPC ................................ A61K 51/00; A61K 45/06
See application file for complete search history.

(56) References Cited

U.S. PATENT DOCUMENTS

| | | | |
|---|---|---|---|
| 4,925,649 A | 5/1990 | Counsell et al. | |
| 4,965,391 A | 10/1990 | Counsell et al. | |
| 5,087,721 A | 2/1992 | Counsell et al. | |
| 5,347,030 A | 9/1994 | Counsell et al. | |
| 5,369,097 A | 11/1994 | Salari et al. | |
| 5,451,663 A | 9/1995 | Kang et al. | |
| 5,626,654 A | 5/1997 | Breton et al. | |
| 5,795,561 A | 8/1998 | Counsell et al. | |
| 5,965,108 A | 10/1999 | Dean | |
| 6,255,519 B1 | 7/2001 | Counsell et al. | |
| 6,417,384 B1 | 7/2002 | Counsell et al. | |
| 6,503,478 B2 | 1/2003 | Chaiken et al. | |
| 7,041,859 B1 | 5/2006 | Kabalka | |
| 7,220,539 B1 | 5/2007 | Du et al. | |
| 7,632,644 B2 | 12/2009 | Weichert et al. | |
| 7,700,075 B2 | 4/2010 | Weichert et al. | |
| 7,893,286 B2 | 2/2011 | Pinchuk et al. | |
| 8,022,235 B2 | 9/2011 | Pinchuk et al. | |
| 8,535,641 B2 | 9/2013 | Weichert et al. | |
| 8,540,968 B2 | 9/2013 | Weichert et al. | |
| 8,835,506 B2 | 9/2014 | Thompson et al. | |
| 8,877,159 B2 | 11/2014 | Weichert et al. | |
| 8,877,160 B2 | 11/2014 | Weichert et al. | |
| 2002/0065429 A1 | 5/2002 | Counsell et al. | |
| 2005/0196339 A1 | 9/2005 | Weichert et al. | |
| 2006/0013767 A1 | 1/2006 | Weichert et al. | |
| 2006/0115426 A1 | 6/2006 | Weichert et al. | |
| 2006/0228298 A1 | 10/2006 | Weichert et al. | |
| 2007/0020178 A1 | 1/2007 | Weichert et al. | |
| 2007/0098633 A2 | 5/2007 | Weichert et al. | |
| 2008/0075660 A1 | 3/2008 | Weichert et al. | |
| 2008/0207492 A1 | 8/2008 | Polt et al. | |
| 2008/0312459 A1 | 12/2008 | Pinchuk et al. | |
| 2010/0316567 A1 | 12/2010 | Weichert et al. | |
| 2011/0064660 A1 | 3/2011 | Pinchuk et al. | |
| 2011/0064661 A1 | 3/2011 | Pinchuk et al. | |
| 2011/0286922 A1* | 11/2011 | Cuthbertson | ......... A61K 51/04 424/1.89 |
| 2012/0156133 A1 | 6/2012 | Pinchuk et al. | |
| 2014/0023587 A1 | 1/2014 | Weichert et al. | |
| 2014/0030187 A1 | 1/2014 | Weichert et al. | |
| 2015/0030538 A1 | 1/2015 | Weichert et al. | |
| 2015/0093330 A1 | 4/2015 | Weichert et al. | |

FOREIGN PATENT DOCUMENTS

| | | |
|---|---|---|
| CA | 2276284 | 6/1998 |
| JP | 2003503355 | 1/2003 |
| JP | 2003088366 | 3/2003 |
| JP | 2005532343 | 10/2005 |
| JP | 2007528374 | 10/2007 |
| JP | 2008545614 | 12/2008 |
| WO | WO98/24480 | 6/1998 |
| WO | WO9824480 | * 6/1998 |
| WO | WO01/00220 | 1/2001 |
| WO | WO03/101495 | 12/2003 |

(Continued)

OTHER PUBLICATIONS

[No Author Listed] "Therapy" Stedman's Medical Dictionary 27th Edition. Lippincott Williams & Wilkins. 2000. Last accessed on Oct. 19, 2009 at http://www.thomsonhc.com.pdrel/librarian/PFDefaultActionId . . . 11 pages.

(Continued)

*Primary Examiner* — Michael G Hartley
*Assistant Examiner* — Jagadishwar R Samala
(74) *Attorney, Agent, or Firm* — Michael Best & Friedrich LLP

(57) ABSTRACT

Methods and compositions utilizing ether and alkyl phospholipid ether analog compounds for treating cancer and imaging, monitoring, and detecting cancer stem cells in humans.

4 Claims, No Drawings

(56) References Cited

FOREIGN PATENT DOCUMENTS

| WO | WO2005/028681 | 3/2005 |
|---|---|---|
| WO | WO2005/063774 | 7/2005 |
| WO | WO2005/084716 | 9/2005 |
| WO | WO2006/014589 | 2/2006 |
| WO | WO2007/013894 | 2/2007 |
| WO | WO2009/005509 | 1/2009 |
| WO | 2010/048144 | 4/2010 |
| WO | 2010/132428 | 11/2010 |

OTHER PUBLICATIONS

[No Author Listed] Database Registry RN 208986-86-9 Jul. 26, 1998. 1 page.
[No Author Listed] Iodine. The Merck Index. Merck & Co., Inc. 1989:794.
[No Author Listed] Synthesis and evaluation of radioiodinated phospholipid ethers for imaging of prostate cancer. Quart J Nucl Med. 1997;41(Suppl 1 to No. 2):14-6.
[No Authors Listed] Modulation of fluorouracil by leucovorin in patients with advanced colorectal cancer: evidence in terms of response rate. Advanced Colorectal Cancer Meta-Analysis Project. J Clin Oncol. Jun. 1992;10(6):896-903.
Arthur et al., The inhibition of cell signaling pathways by antitumor ether lipids. Biochim Biophys Acta. Feb. 5, 1998;1390(1):85-102.
Australian Office Action for Application No. 2005-269861 dated Jan. 13, 2010.
Bao et al., Glioma stem cells promote radioresistance by preferential activation of the DNA damage response. Nature. Dec. 7, 2006;444(7120):756-60. Epub Oct. 18, 2006.
Becher et al., Phase II Trial of Orally Administered Miltefosine in Advanced Colorectal Cancer. Onkologie. 1993;16:11-5.
Beitler et al., Close or positive margins after surgical resection for the head and neck cancer patient: the addition of brachytherapy improves local control. Int J Radiat Oncol Biol Phys. Jan. 15, 1998;40(2):313-7.
Berdel et al., Daily Oral Miltefosine (Hexadecy Phosphocholin) in Patients with Advanced Non-Small Cell Lung Cancer. A Phase II Study. Onkologie. 1992;15:238-42.
Brownstein, Clinical Experience with Inorganic, Non-radioactive Iodine-Iodide. The Original Internist. 2005:105-8.
Buchsbaum et al., Improved delivery of radiolabeled anti-B1 monoclonal antibody to Raji lymphoma xenografts by predosing with unlabeled anti-B1 monoclonal antibody. Cancer Res. Feb. 1, 1992; 52:637-642.
Canadian Office Action for Application No. 2557698 dated Dec. 8, 2010.
Chekenya et al., The progenitor cell marker NG2/MPG promotes chemoresistance by activation of integrin-dependent PI3K/Akt signaling. Oncogene. Sep. 4, 2008;27(39):5182-94. Epub May 12, 2008.
Chia et al., Aberrations in Phospholipase D Activity-A Pharmacological Target for Cancer Detection. The FASEB Journal. 2006;20:A488. Abstract 330.10.
Chinese Office Action for Application No. 200580007056.9 dated Mar. 6, 2009.
Chinese Office Action for Application No. 200580026935.6 dated May 8, 2009.
Chinese Office Action for Application No. 200580026935.6 dated Nov. 27, 2009.
Christopher H. Crane et al., Combining Gemcitabine with Radiation in pancreatic Cancer: Understanding Important Variables Influencing the Therapeutic Index, Seminars in Oncology, vol. 28(3), 25-33, 2001.
Clezy et al., The Chemistry of Pyrrolic Compounds. VIII. Dipyrrythiones. Aust J Chem. 1969;22:239-49.
Counsell et al, Isotope Production and Applications in the 21st Century, Proceedings of the International Conference on Isotopes, 3rd, Vancouver, BC, Canada, Sep. 6-10, 1999 (2000), Meeting Date 1999, 163-166.

Counsell et al., Tumor visualization with a radioiodinated phospholipid ether. J Nucl Med. Mar. 1990;31(3):332-6.
Curley et al., Radiofrequency ablation of unresectable primary and metastatic hepatic malignancies: results in 123 patients. Ann Surg. Jul. 1999;230(1):1-8.
De Gramont et al., Randomized trial comparing monthly low-dose leucovorin and fluorouracil bolus with bimonthly high-dose leucovorin and fluorouracil bolus plus continuous infusion for advanced colorectal cancer: a French intergroup study. J Clin Oncol. Feb. 1997;15(2):808-15.
De Santes et al., Radiolabeled antibody targeting of the HER-2/neu oncoprotein. Cancer Research. Apr. 1, 1992;52:1916-23.
Endo, Development of radiation therapy for cancers. Experimental Medicine. 2004;22(14):208-12.
Eramo et al., Chemotherapy resistance of glioblastoma stem cells. Cell Death Differ. Jul. 2006;13(7):1238-41. Epub Feb. 3, 2006.
European Intention to Grant for Application No. EP 08010321.1 dated Aug. 5, 2013.
European Office Action for Application No. 05729873.9 dated Apr. 26, 2007.
European Office Action for Application No. 05729873.9 dated Jun. 16, 2008.
European Office Action for Application No. 05729873.9 dated Mar. 23, 2009.
European Office Action for Application No. 05769481.2 dated Dec. 21, 2007.
European Office Action for Application No. 05858499.6 dated Oct. 9, 2007.
European Office Action for Application No. 08010321.1 dated May 8, 2012.
European Office Action for Application No. 08020805.1 dated May 3, 2012.
Extended European Search Report for Application No. EP 08010321.1 dated Oct. 6, 2009.
Extended European Search Report for Application No. EP 08020805.1 dated Jul. 14, 2009.
Fong et al., Clinical score for predicting recurrence after hepatic resection for metastatic colorectal cancer: analysis of 1001 consecutive cases. Ann Surg. Sep. 1999;230(3):309-18; discussion 318-21.
Fuwa et al., The clinical utility of 192 iridium endobronchial irradiation for lung cancer. Jpn J Cancer Clin. 1995;41(12):1437-42. (The year of publication is sufficiently earlier than the effective U.S. filing date and any foreign priority date so that the particular month of publication is not in issue, See MPEP 609.04(a)).
Giacchetti et al., Phase III multicenter randomized trial of oxaliplatin added to chronomodulated fluorouracil-leucovorin as first-line treatment of metastatic colorectal cancer. J Clin Oncol. Jan. 2000;18(1):136-47.
Golub et al., Molecular classification of cancer: class discovery and class prediction by gene expression monitoring. Science. Oct. 15, 1999;286(5439):531-7.
Goud et al., Synthesis of 8-heteroatom-substituted 4,4-difluoro-4-bora-3a, 4a-diaza-s-indacene dyes (BODIPY). Tetrahedron. 2006;62:5084-91.
Graff et al., Increased AKT activity contributes to prostate cancer progression by dramatically accelerating prostate tumor growth and diminishing p27Kip1 expression. J Biol Chem. Aug. 11, 2000; 275:24500-24505.
Greven et al., Can positron emission tomography distinguish tumor recurrence from irradiation sequelae in patients treated for larynx cancer? Cancer J Sci Am. Nov.-Dec. 1997;3(6):353-7.
Hu et al., Targeting cancer stem cells: a new therapy to cure cancer patients. Am J Cancer Res. 2012;2(3):340-56. Epub Apr. 28, 2012.
Hunt et al., Assessment of the aggregation state of integral membrane proteins in reconstituted phospholipid vesicles using small angle neutron scattering. J Mol Biol. Nov. 14, 1997;273(5):1004-19.
Ike et al., Results of aggressive resection of hung metastases from colorectal carcinoma detected by intensive follow-up. Dis Colon Rectum. Apr. 2002;45(4):468-73; discussion 473-5.
Imboden et al., The level of MHC class I expression on murine adenocarcinoma can change the antitumor effector mechanism of immunocytokine therapy. Cancer Res. Feb. 15, 2001;61(4):1500-7.

(56) References Cited

OTHER PUBLICATIONS

Indian Office Action for Application No. 4875/DELNP/2006 dated Jun. 7, 2011.
International Preliminary Report on Patentability for Application No. PCT/US2005/006681 dated Sep. 14, 2006.
International Preliminary Report on Patentability for Application No. PCT/US2005/024259 dated Jan. 18, 2007.
International Preliminary Report on Patentability for Application No. PCT/US2005/047657 dated Jul. 5, 2007.
International Preliminary Report on Patentability for Application No. PCT/US2007/017885 dated Feb. 26, 2009.
International Preliminary Report on Patentability for Application No. PCT/US2010/038294 dated Feb. 13, 2014.
International Preliminary Report on Patentability for Application No. PCT/US2010/048340 dated Mar. 22, 2012.
International Preliminary Report on Patentability for Application No. PCT/US2010/048351 dated Feb. 20, 2014.
International Search Report and Written Opinion for Application No. PCT/US2005/006681 dated Feb. 20, 2006.
International Search Report and Written Opinion for Application No. PCT/US2005/024259 dated Mar. 1, 2006.
International Search Report and Written Opinion for Application No. PCT/US2005/047657 dated Jan. 22, 2007.
International Search Report and Written Opinion for Application No. PCT/US2010/048340 dated Oct. 14, 2010.
International Search Report and Written Opinion for Application No. PCT/US2010/048351 dated Oct. 19, 2010.
International Search Report for Application No. PCT/US2007/017885 dated Aug. 14, 2008.
Invitation to Pay Additional Fees for Application No. PCT/US2005/006681 dated Nov. 8, 2005.
Invitation to Pay Additional Fees for Application No. PCT/US2010/038294 dated Jul. 23, 2010.
Israeli Office Action for Application No. 177645 dated Aug. 13, 2009.
Israeli Office Action for Application No. 177645 dated May 13, 2010.
Israeli Office Action for Application No. 180363 dated Sep. 13, 2009.
Japanese Office Action dated Jul. 29, 2014 for Application No. JP 2012-515178.
Japanese Office Action for Application No. 2007-501917 dated Dec. 7, 2010.
Japanese Office Action for Application No. 2007-501917 dated Sep. 13, 2011.
Japanese Office Action for Application No. JP 2012-005213 dated Jul. 23, 2013.
Japanese Office Action for Application No. JP 2012-005213 dated Mar. 18, 2014.
Japanese Office Action for Application No. JP 2012-234608 dated Nov. 19, 2013.
Japanese Office Action dated Mar. 3, 2015 for Application No. JP2012-234608.
Japanese Office Action dated Sep. 2, 2014 for Application No. JP 2012-234608.
Japanese Office Action dated Sep. 26, 2014 for Application No. JP 2012-528915.
Jhanwar et al., Current status of therapy of solid tumors. J Nucl Med. Jan. 2005;46 Suppl 1:141S-50S.
Johannessen et al., Highly infiltrative brain tumours show reduced chemosensitivity associated with a stem cell-like phenotype. Neuropathol Appl Neurobiol. Aug. 2009;35(4):380-93.
Jurcic et al., Radiolabeled anti-CD33 monoclonal antibody M195 for myeloid leukemias. Radiolabeled anti-CD33 monoclonal antibody M195 for myeloid leukemias. Cancer Res. Dec. 1, 1995;55(23 Suppl):5908s-5910s.
Kallman, Commentary on Part 5. In: Rodent tumor models in experimental cancer therapy. Pergamon Press. New York. 1987:111-32.
Kamigaki et al., Therapy and imaging of pancreatic carcinoma xenografts with radioiodine-labeled chimeric monoclonal antibody A10 and its Fab fragment. Jpn J Cancer Res. Dec. 1995;86(12):1216-23.
Kuerschner et al., Polyene-lipids: a new tool to image lipids. Nat Methods. Jan. 2005;2(1):39-45. Epub Dec. 21, 2004.
Kuo et al., Imaging of stem cell-derived gliomas with 1241-NM404. CMR2009: 9.01. Abstract. Contrast Media Mol Imaging. Nov./Dec. 2009;4(6):286.
Lencioni et al., Percutaneous radiofrequency thermal ablation of liver malignancies: techniques, indications, imaging findings, and clinical results. Abdom Imaging. Jul.-Aug. 2001;26(4):345-60.
Liebeskind et al., Heteroaromatic thioether-boronic acid cross-coupling under neutral reaction conditions. Org Lett. Mar. 21, 2002;4(6):979-81.
Liu et al., Analysis of gene expression and chemoresistance of CD133+ cancer stem cells in glioblastoma. Mol Cancer. Dec. 2, 2006;5:67.
Longino et al., Preliminary Clinical Imaging and Pharmacokinetic Results with NM404 in Non-Small Cell Lung Cancer. Presentation abstract. Presented at the 5th International Symposium on Radiohalogens meeting in Whistler, B.C. Sep. 11-15, 2004. Last accessed on Jul. 13, 2011 at http://legacyweb.triumf.ca/5ISR/5ISR%20Abstracts.pdf.
Longino et al., Preliminary Clinical Imaging and Pharmacokinetic Results with NM404 in Non-Small Cell Lung Cancer. Presented at the 5th International Symposium on Radiohalogens meeting in Whistler, B.C. Sep. 11-15. Slideshow presentation on Sep. 15, 2004. Last accessed on Jul. 13, 2011 at http://legacyweb.triumf.ca/5ISR/44/-CS29-NM404%20Imaging%20&%20PK-.pdf. 20 pages.
Longino, M.A. et al., Tumor Selective Retention of NM404—Involvement of Phospholipase D. Molecular Imag. 2004;3(3). Abstract ID 290.
Maier et al., Fluorescent lipid probes: some properties and applications (a review). Chem Phys Lipids. Jun. 2002;116(1-2):3-18.
Malik et al., Cancer stem cells and resistance to chemo and radio therapy. Front Biosci. Jan. 1, 2012;4:2142-9. Review.
Mayr et al., Method and timing of tumor volume measurement for outcome prediction in cervical cancer using magnetic resonance imaging. Int J Radiat Oncol Biol Phys. Jan. 1, 2002;52(1):14-22.
Mexican Office Action for Application No. MX/a/2007/007497 dated Apr. 5, 2010.
Mexican Office Action for Application No. PA/a/2006/009681 dated Nov. 20, 2008.
Meyer et al., Potential tumor or organ-imaging agents. 30. Radioiodinated phospholipid ethers. J Med Chem. Sep. 1989;32(9):2142-7.
Miyagawa et al., Imaging of HSV-tk Reporter gene expression: comparison between [18F]FEAU, [18F]FFLAU, and other imaging probes. J Nucl Med. Apr. 2008;49(4):637-48. Epub Mar. 14, 2008.
Murray et al., Phase II radioimmunotherapy trial with 131I-CC49 in colorectal cancer. Cancer. Feb. 1, 1994;73(3 Suppl):1057-66.
MV Blagosklonny, Target for cancer therapy: Proliferating cells or stem cells, Leukemia, 20, 385-391, 2006.
Nakabeppu et al., Radionuclide therapy of malignant pheochromocytoma with 131I-MIBG. Ann Nucl Med. Nov. 1994;8(4):259-68.
New Zealand Office Action for Application No. 549562 dated Dec. 1, 2009.
New Zealand Office Action for Application No. 549562 dated Jan. 12, 2010.
New Zealand Office Action for Application No. 549562 dated Mar. 5, 2009.
New Zealand Office Action for Application No. 549562 dated Sep. 23, 2009.
New Zealand Office Action for Application No. 552914 dated Apr. 24, 2009.
New Zealand Office Action for Application No. 552914 dated Dec. 2, 2009.
New Zealand Office Action for Application No. 552914 dated Nov. 17, 2009.

(56) References Cited

OTHER PUBLICATIONS

Nijsen et al., Radioactive holmium loaded poly(L-lactic acid) microspheres for treatment of hepatic malignancies: efficacy in rabbits. Thesis. 2001. Chapter 7. pp. 109-122. (The year of publication is sufficiently earlier than the effective U.S. filing date and any foreign priority date so that the particular month of publication is not in issue. See MPEP 609.04(a)).
Noh et al., Overexpression of phospholipase D1 in human breast cancer tissues. Cancer Lett. Dec. 20, 2000;161(2):207-14. Abstract only.
Notice of Allowance for U.S. Appl. No. 11/177,749 dated Nov. 23, 2009.
Notice of Allowance for U.S. Appl. No. 11/382,645 dated Sep. 24, 2009.
Notice of Allowance for U.S. Appl. No. 12/156,287 dated Oct. 12, 2010.
O'Dwyer et al., Follow-up of stage B and C colorectal cancer in the United States and France. Semin Oncol. Feb. 2001;28(1 Suppl 1):45-9.
Office Communication for U.S. Appl. No. 10/906,687 dated Apr. 21, 2010.
Office Communication for U.S. Appl. No. 10/906,687 dated Dec. 19, 2012.
Office Communication for U.S. Appl. No. 10/906,687 dated Jul. 10, 2013.
Office Communication for U.S. Appl. No. 10/906,687 dated Mar. 16, 2009.
Office Communication for U.S. Appl. No. 10/906,687 dated May 24, 2011.
Office Communication for U.S. Appl. No. 10/906,687 dated Nov. 2, 2009.
Office Communication for U.S. Appl. No. 10/906,687 dated Oct. 5, 2010.
Office Communication for U.S. Appl. No. 11/177,749 dated Apr. 1, 2009.
Office Communication for U.S. Appl. No. 11/316,620 dated Apr. 2, 2009.
Office Communication for U.S. Appl. No. 11/316,620 dated Apr. 29, 2013.
Office Communication for U.S. Appl. No. 11/316,620 dated Dec. 21, 2012.
Office Communication for U.S. Appl. No. 11/316,620 dated Jun. 22, 2010.
Office Communication for U.S. Appl. No. 11/316,620 dated Mar. 10, 2011.
Office Communication for U.S. Appl. No. 11/316,620 dated Nov. 12, 2009.
Office Communication for U.S. Appl. No. 11/316,620 dated Oct. 13, 2011.
Office Communication for U.S. Appl. No. 11/382,645 dated Apr. 22, 2009.
Office Communication for U.S. Appl. No. 11/671,403 dated Apr. 6, 2009.
Office Communication for U.S. Appl. No. 11/891,939 dated Dec. 3, 2008.
Office Communication for U.S. Appl. No. 12/813,992 dated Feb. 28, 2013.
Office Communication for U.S. Appl. No. 12/813,992 dated Jul. 27, 2012.
Office Communication for U.S. Appl. No. 12/813,992 dated May 13, 2014.
Office Communication for U.S. Appl. No. 12/879,093 dated May 3, 2012.
Office Communication for U.S. Appl. No. 12/879,167 dated Oct. 5, 2012.
Office Communication for U.S. Appl. No. 13/403,445 dated Jan. 26, 2015.
Office Communication for U.S. Appl. No. 13/403,445 dated May 9, 2013.
Office Communication for U.S. Appl. No. 13/403,445 dated Oct. 3, 2012.
Office Communication for U.S. Appl. No. 13/964,315 dated Dec. 2, 2013.
Office Communication for U.S. Appl. No. 13/964,315 dated Jun. 24, 2014.
Office Communication for U.S. Appl. No. 13/964,315 dated Mar. 13, 2014.
Office Communication for U.S. Appl. No. 13/964,380 dated Dec. 16, 2013.
Office Communication for U.S. Appl. No. 13/964,380 dated Jun. 4, 2014.
Oshimoto et al., Increased activity and expression of phospholipase D2 in human colorectal cancer. Oncol Res. 2003;14(1):31-7. Abstract only. 4 pages.
Page et al., Elevated phosphorylation of AKT and Stat3 in prostate, breast, and cervical cancer cells. Int J Oncol. Jul. 2000; 17:23-28.
Partial European Search Report for Application No. EP 08010321.1 dated Jul. 13, 2009.
Penna et al., Colorectal metastasis (liver and lung). Surg Clin North Am. Oct. 2002;82(5):1075-90, x-xi.
Pickhardt et al., Computed tomographic virtual colonoscopy to screen for colorectal neoplasia in asymptomatic adults. N Engl J Med. Dec. 4, 2003;349(23):2191-200. Epub Dec. 1, 2003.
Pickhardt et al., Microcomputed tomography colonography for polyp detection in an in vivo mouse tumor model. Proc Natl Acad Sci U S A. Mar. 1, 2005;102(9):3419-22. Epub Feb. 22, 2005.
Pinchuk et al., Synthesis and structure-activity relationship effects on the tumor avidity of radioiodinated phospholipid ether analogues. J Med Chem. Apr. 6, 2006;49(7):2155-65.
Plotzke et al., Biodistribution, metabolism, and excretion of radioiodinated phospholipid ether analogs in tumor-bearing rats. J Nucl Biol Med. Dec. 1993;37(4):264-72.
Plotzke et al., Selective localization of radioiodinated alkylphosphocholine derivatives in tumors. Int J Rad Appl Instrum B. Oct. 1992;19(7):765-73.
Plotzke et. al., Selective localization of a radioiodinated phospholipid ether analog in human tumor xenografts. J Nucl Med. May 1993;34(5):787-92.
Quon, et al., "Flying through" and "flying around" a PET/CT scan: Pilot study and development of 3D integrated 18F-FDG PET/CT for virtual bronchoscopy and colonoscopy. J Nucl Med. Jul. 2006;47(7):1081-7.
Rampy et al. Synthesis and biological evaluation of radioiodinated phospholipid ether analogs. Nucl Med Biol. May 1995;22(4):505-12.
Rampy et al., Biological disposition and imaging of a radioiodinated alkylphosphocholine in two rodent models of breast cancer. J Nucl Med. Sep. 1996;37(9):1540-5.
Rampy et al., Synthesis and biological evaluation of radioiodinated phospholipid ether stereoisomers. J Med Chem. Aug. 4, 1995;38(16):3156-62.
Ricardo Pardal et al. Applying the principles of stem-cell biology to cancer, Nature, vol. 3, 895-902, 2003.
Rich, Cancer stem cells in radiation resistance. Cancer Res. Oct. 1, 2007;67(19):8980-4.
Saltz et al., Irinotecan plus fluorouracil and leucovorin for metastatic colorectal cancer. Irinotecan Study Group. N Engl J Med. Sep. 28, 2000;343(13):905-14.
Sandgren et al., Evaluation of 125I-NM404 in a Spontaneous Murine Pancreatic Adenocarcinoma Model. Aug. 2003, 2nd Annual Meeting of the Society of Molecular Imaging.
Sik Min et al., Neoplastic transformation and tumorigenesis associated with overexpression of phospholipase D isozymes in cultured murine fibroblasts. Carcinogenesis. Oct. 2001;22(10):1641-7.
Snyder et al., Alkyl and alk-l-enyl ethers of glycerol in lipids from normal and neoplastic human tissues. Cancer Res. Jan. 1969;29(1):251-7.
Snyder et al., Occurrence and nature of O-alkyl and O-alk-l-enyl moieties of glycerol in lipids of Morris transplanted hepatomas and normal rat liver. Biochim Biophys Acta. Apr. 29, 1969;176(3):502-10.

(56) References Cited

OTHER PUBLICATIONS

Solbiati et al., Percutaneous radio-frequency ablation of hepatic metastases from colorectal cancer: long-term results in 117 patients. Radiology. Oct. 2001;221(1):159-66.
Stahl et al., PET/CT molecular imaging in abdominal oncology. Abdom Imaging. May-Jun. 2004;29(3):388-97.
Summons to Attend Oral Proc for Application No. 05729873.9 dated Jan. 22, 2008.
Terwogt et al., Phase II trial of topically applied miltefosine solution in patients with skin-metastasized breast cancer. Br J Cancer. Mar. 1999;79(7-8):1158-61.
Wagner et al., Boron-dipyrromethene dyes for incorporation in synthetic multi-pigment light-harvesting arrays. Pure & Appl Chem. 1996;68(7):1373-80.
Wang et al., An efficient synthesis of .delta.-aminolevulinic acid (ALA) and its isotopomers. Tetrahedron Letters. 1997;38(5):739-40. (The year of publication is sufficiently earlier than the effective U.S. filing date and any foreign priority date so that the particular month of publication is not in issue. See MPEP 609.04(a)).
Wang et al., Molecular imaging with 123I-FIAU, 18F-FUdR, 18F-FET, and 18F-FDG for monitoring herpes simplex virus type 1 thymidine kinase and ganciclovir prodrug activation gene therapy of cancer. J Nucl Med. Jul. 2006;47(7):1161-71.
Weber et al., Interleukin-12 gene transfer results in CD8-dependent regression of murine CT26 liver tumors. Ann Surg Oncol. Mar. 1999;6(2):186-94.
Weichert et al., Evaluation of 125I-NM404 in a spontaneous murine pancreatic adenocarcinoma model. 2nd Annual Meeting of the Society of Molecular Imaging. San Francisco, USA. Aug. 15-18, 2003. Presentation No. 304. Abstract only. 1 page. Retrieved from the Internet on Jan. 27, 2006 at http://www.abstractsonline.com/viewer/viewAbstract.asp?CKey={A174CAD4-- 4C67-46EE-97CA-B94654C77699}&MKey={4C56C7C9-3CB4-404E-A0C1-3F37525A5245}&A-Key={A4C6DD8F-4BF2-400D-97ED-20C14381CDBB}&SKey={0AAB7B18-F58E-4226-A5D5-7-55F3585A60F}>.
Weichert et al., Initial Clinical Imagining Results with NM404 in Non-Small Cell Lung Cancer. Molec Imag. 2004;3(3):269-70.
Weichert et al., Polyiodinated triglyceride analogs as potential computed tomography imaging agents for the liver. J Med Chem. Feb. 17, 1995;38(4):636-46.
Weichert et al., Radioiodination via Isotope Exchange in Pivalic Acid. Appl Radiat Isot. 1986;37(8):907-13.
Weichert et al., Specificity of NM404 for Hyperplasia versus Neoplasia in the ApcMin/+ Endogenous Mammary Adenocarcinoma Model. 2.sup. nd Annual Meeting of the Society of Molecular Imaging. San Francisco. Aug. 15-18, 2003. Presentation No. 305. Abstract only. 1 page. Retrieved from the Internet on Jan. 27, 2006 at http://www.abstractsonline.com/viewer/viewAbstract.asp?CKey={175C0489-C80- 8-47DF-B4EF-5CF57EE52265} &MKey={4C56C7C9-3CB4-404E-A0C1-3F37525A5245}&AKey={A4C6DD8F-4BF2-400D-97E-D-20C14381CDBB}&SKey={0AAB7B18-F58E-4226-A5DF-755F3585A60F}.
Weichert, Noninvasive Evaluation of Colon Tumors in Live Mice using MicroCT Virtual colonoscopy. Academy of Molecular Imaging Meetings-Orlando. Mar. 18-23, 2005. Presented on Mar. 22, 2005. Slideshow presentation. 40 pages.
Wichmann et al., Carcinoembryonic antigen for the detection of recurrent disease following curative resection of colorectal cancer. Anticancer Res. Nov.-Dec. 2000;20(6D):4953-5.
Written Opinion for Application No. PCT/US2007/017885 dated Jul. 31, 2008.
Zasadny et al., Predicted dosimetry for I-131-NM-404, a phospholipid ether agent for tumor imaging and possible therapy. J Nucl Med. 1999;40(5):39P.
Diehn et al., "Therapeutic Implications of the Cancer Stem Cell Hypothesis," Seminars in Radiation Oncology, 2009, vol. 19, No. 2, pp. 78-86.
European Patent Office Action for Application No. 10786904.2 dated Jan. 9, 2018 (6 pages).
Tang et al., "Cancer stem cell: target for anti-cancer therapy," The Faseb Journal, 2007, vol. 21, No. 14, pp. 3777-3785.

\* cited by examiner

ETHER AND ALKYL PHOSPHOLIPID COMPOUNDS FOR TREATING CANCER AND IMAGING AND DETECTION OF CANCER

CROSS-REFERENCE TO RELATED APPLICATIONS

This application is a continuation of U.S. application Ser. No. 13/887,981 filed on May 6, 2013, now U.S. Pat. No. 9,339,564, which is a continuation of U.S. application Ser. No. 12/813,992 filed on Jun. 11, 2010, now abandoned, which claims priority to U.S. Provisional Application No. 61/186,600 filed on Jun. 12, 2009.

BACKGROUND OF THE INVENTION

Stem cells, which possess the unique ability to undergo self-renewal and differentiation into tissue-specific cells, give rise to all tissues in the body. Unlike embryonic stem cells which can differentiate into many different cell types, tissue specific stem cells can only form cells unique to one tissue. Recent advances in stem cell molecular biology techniques have enabled researchers to examine the concept that a malignant tumor can be formed and maintained due to the presence of a small number of cancer-specific stem cells.

Stem cells can renew themselves. This self-renewal process of all stem cells, including tumor stem cells, is known to be very tightly regulated. Many reports in the past several years have confirmed that small populations of cancer stem cells have been found in a variety of cancers including glioma, breast, pancreas, ovarian, hepatocellular carcinoma, and melanoma, to name a few. Furthermore, it has also been widely reported that current cancer chemotherapeutic agents which can successfully kill differentiated tumor cells are actually ineffective against the small population of cancer stem cells which may be a contributing factor to the regeneration of cancer cells after chemotherapy. These agents act by inhibiting a wide variety of known cell signaling, growth regulation, and cell death mechanisms within these normally differentiated cancer cells. Several studies have suggested that long-term ineffectiveness of chemotherapy agents against cancer stem cells may be due to their lack of penetration into these cells. Although early in development, this hypothesis may at least partially explain the regeneration of tumor cells after chemotherapy.

Because of its nature, radiation may afford a higher degree of efficacy in killing cancer stem cells. Although certain tumors can be effectively treated with external beam radiation, in many cases, the tumors reappear at a later time. In addition to chemo-resistance of cancer stem cells, it is now known that glioma stem cells are also 30% more radio-resistant than regular glioma cells. This finding is based on radiation applied via external beam. Systemically administered radiotherapeutics that can target normally differentiated cancer cells may still hold a significant advantage over chemotherapeutics due to their collateral killing ability, wherein radiation emanating from surrounding tumor cells has the ability to kill a lone stem cell via a "cross-fire" effect (The "cross-fire" effect is a theory that the radioactive compounds can kill both the cancer cells to which they attach and the adjacent tumor cells).

In addition, systemically administered radiotherapy gives a prolonged and continuous radiation exposure which appears to be more effective in tumor cell killing than is intermittent external radiation therapy. It is even more probable that if a systemically administered radiotherapeutic agent could actually target the cancer stem cells and penetrate their membrane, the radiotherapeutic agent would have a better chance of killing the cancer stem cell and preventing its eventual regrowth.

Accordingly, there is a need for radiotherapeutic agents that can treat cancer either by themselves or in combination with external beam radiotherapy. In addition, there is a need for new methods of identifying stem cells, both in vitro and in vivo.

BRIEF SUMMARY OF THE INVENTION

In one aspect, this invention relates to a method of treating cancer comprising administering to a patient in need thereof a therapeutically effective amount of a radiolabeled ether or alkyl phospholipid compound of Formula I

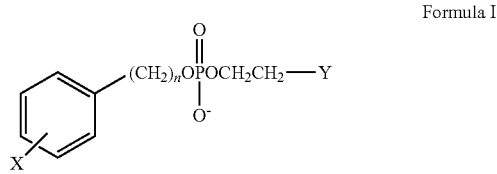

Formula I where X is an isotope of iodine; n is an integer between 12 and 30; and Y is selected from the group comprising $N^+H_3$, $HN^+(R)_2$, $N^+H_2R$, and $N^+(R)_3$, wherein R is an alkyl or arylalkyl substituent, or Formula II

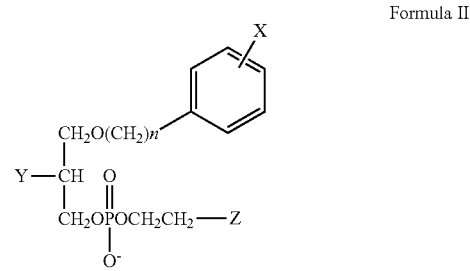

Formula II where X is an isotope of iodine; n is an integer between 12 and 30; Y is selected from the group consisting of H, OH, COOH, COOR and OR, and Z is selected from the group comprising $N^+H_3$, $HN^+(R)_2$, $N^+H_2R$, and $N^+(R)_3$, wherein R is an alkyl or arylalkyl substituent, wherein said therapeutically effective amount of said radiolabeled ether or alkyl phospholipid compound is sufficient to penetrate into said cancer stem cells and wherein a population of said cancer stem cells is reduced.

The therapeutically effective amount that is sufficient to penetrate into said cancer stem cells is preferably between 0.21-21 mg (equivalent to a 7-700 mCi, total mass dose range) and between 0.03-0.21 mg/kg (equivalent to 1-7 mCi/kg, by weight dose range).

For a therapy in humans, a preferred isotope of iodine is $^{131}I$, although other radioactive isotopes, including $^{123}I$, $^{124}I$, and $^{125}I$ can also be used.

In one embodiment of the invention, the alkyl phospholipid compound labeled with a nonradioactive ("cold") isotope of iodine (e.g., $^{127}I$) can be utilized to treat cancer stem cells.

In the most preferred embodiment, the radiolabeled compound is CLR1404 (18-(p-iodophenyl)octadecyl phosphocholine) radiolabeled with $^{131}$I.

In addition, ether and alkyl phospholipid compounds having more than one radioactive iodine may be used for the purposes of the present invention. Some representative structures are as follows:

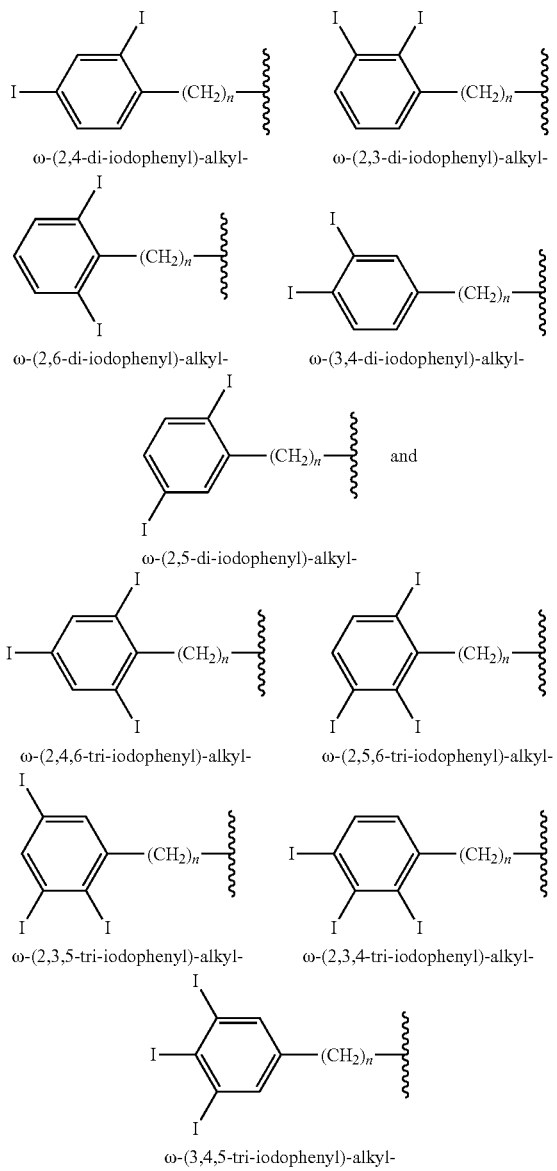

The part of the molecule after the vertical wavy line is the same as in the molecules with one Iodine attached to the phenyl ring.

In one embodiment, the cancer is solid cancer.

In one embodiment, the solid cancers are selected from the group consisting of lung cancer, breast cancer, glioma, squamous cell carcinoma, prostate cancer, melanoma, renal cancer, colorectal cancer, ovarian cancer, pancreatic cancer, sarcoma, and stomach cancer.

In another embodiment, the invention provides pharmaceutical compositions comprising radiolabeled ether or alkyl phospholipid compounds as described in the application formulated for use in the treatment of cancer wherein the radiolabeled ether or alkyl phospholipid compounds penetrate cancer stem cells.

In another embodiment, the invention relates to method of imaging a population of cancer stem cells in vivo comprising administering to a patient in need thereof an effective amount of a radiolabeled ether or alkyl phospholipid compound of Formula I

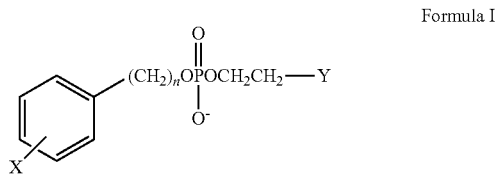

Formula I where X is an isotope of iodine; n is an integer between 12 and 30; and Y is selected from the group comprising $N^+H_3$, $HN^+(R)_2$, $N^+H_2R$, and $N^+(R)_3$, wherein R is an alkyl or arylalkyl substituent,
or Formula II

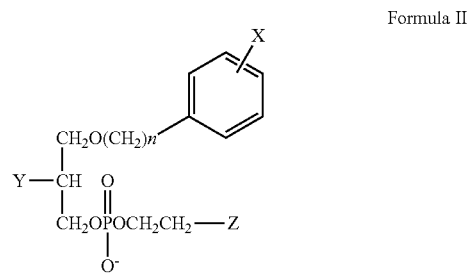

Formula II where X is an isotope of iodine; n is an integer between 12 and 30; Y is selected from the group consisting of H, OH, COOH, COOR and OR, and Z is selected from the group comprising $N^+H_3$, $HN^+(R)_2$, $N^+H_2R$, and $N^+(R)_3$, wherein R is an alkyl or arylalkyl substituent, wherein said radiolabeled ether or alkyl phospholipid compound penetrates said cancer stem cells.

For imaging in humans, a preferred isotope of iodine is $^{124}$I, although other radioactive isotopes, including $^{123}$I and $^{131}$I can be used, too.

In one preferred embodiment, the radiolabeled ether or alkyl phospholipid compound is CLR1404 (18-(p-iodophenyl)octadecyl phosphocholine) radiolabeled with $^{124}$I.

In other embodiments of the invention, fluorescent analogs of PLE compounds may be used in the claimed imaging methods. For example, the invention specifically contemplates the use of CLR1501 compound, which has the following structure:

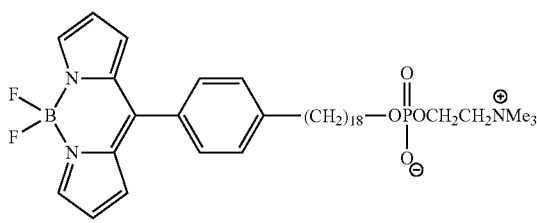

The application specifically incorporates by reference all fluorescent PLE analogs described in the pending patent application Ser. Nos. 12/463,970; 12/463,978; 12/463,983; 12/463,990; and 12/463,998.

The imaging can be performed through a hybrid scanning, utilizing a functional imaging modality, such as single photon emission computed tomography (SPECT) or positron emission tomography (PET) in combination with computed tomography (CT) and/or magnetic resonance imaging (MRI) techniques, and combinations thereof.

In other embodiments, the invention provides methods of ex vivo or in vitro labeling cancer stem cells comprising administering to cells suspected of comprising cancer stem cells an effective amount of a radiolabeled ether or alkyl phospholipid compound of Formula I or II. In other embodiments of the invention, the above-described fluorescent analogs of phospholipid compounds may be used for the labeling.

In other embodiments, the described compounds can be used for identifying cancer stem cells in vivo, by administering the compounds to an animal and then identifying and/or quantifying stem cells of any type in any organ or tissue.

DETAILED DESCRIPTION OF THE INVENTION

We have developed several series of tumor-selective radiolabeled ether and alkyl phospholipid compounds for imaging, characterization, and treatment of malignant tumors. Thus far, the lead compound, CLR1404, has shown striking uptake and prolonged selective retention properties in over fifty solid xenograft and spontaneous human tumor and rodent tumor models. Unlike $^{18}$F-Fluorodeoxyglucose ($^{18}$F-FDG), the current gold standard for oncologic imaging, CLR1404 does not localize in benign or premalignant lesions or in inflammatory lesions. Cellular signaling and regulation of phospholipids, including phospholipase-D and its isoforms, as well as Phosphatase and Tensin Homologue Deleted from Chromosome-10 (PTEN) and phosphatidylinositol phosphate (PIPn) pathways, are known to be directly involved in upstream regulation of many key oncogenic pathways. We now have strong evidence that the uptake and retention of our PLE analogs is due at least in part to these upstream regulation and signaling cancer cell pathways. Other non-radioactive members of the "antitumor alkyl-phospholipid" class of molecules have been shown to induce tumor cell apoptosis through inhibition of AKT-dependent downstream signaling; the very mechanism which is thought to be important in enhancing malignant stem cell survival in response to either chemotherapy or radiation.

This invention relates to a discovery that the unique properties of ether and alkyl phospholipid compounds, especially CLR1404, including their prolonged selective retention in malignant cells, and their ability to inhibit AKT-dependent survival mechanisms, can be utilized to treat and/or detect cancer stem cells.

For purposes of the present invention, the terms "PLE compounds" and "PLE analogs" are interchangeable and refer to ether and alkyl phospholipid compounds as described in the invention.

For purposes of the present invention, the term "treating" refers to reversing, alleviating, inhibiting, or slowing the progress of the disease, disorder, or condition to which such term applies, or one or more symptoms of such disease, disorder, or condition.

The term "cancer stem cell" refers to a cell with tumor-initiating and tumor-sustaining capacity.

The term "therapeutically effective amount" refers to a sufficient amount of the compound to reduce the number of cancer stem cells. It will be understood, however, that the total daily usage of the compounds and compositions of the present invention will be decided by the attending physician within the scope of sound medical judgment. The specific therapeutically effective dose level for any particular patient will depend upon a variety of factors including the specific cancer being treated, the stage of the cancer, activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "crystalline forms" and related terms herein refers to the various crystalline modifications of a given substance, including, but not limited to, polymorphs, solvates, hydrates, co-crystals and other molecular complexes, as well as salts, solvates of salts, hydrates of salts, other molecular complexes of salts, and polymorphs thereof.

The compounds of the invention encompass any deuterated versions of the compounds.

The compounds of the invention may exist in different isomeric (e.g. enantiomers and diastereoisomers) and enol forms. The invention contemplates all such isomers, both in pure form and in admixture, including racemic mixtures.

The compounds of the invention encompass pharmaceutically acceptable salts of the phosphocholine portion of the compounds. The compounds of the invention are also preferably inner salts (zwitterions) themselves.

The term "pharmaceutically acceptable salts" is meant to include salts of active compounds which are prepared with relatively nontoxic acids. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)).

As used herein, a salt or polymorph that is "pure," i.e., substantially free of other polymorphs, contains less than about 10% of one or more other polymorphs, preferably less than about 5% of one or more other polymorphs, more preferably less than about 3% of one or more other polymorphs, most preferably less than about 1% of one or more other polymorphs.

The terms, "polymorphs" and "polymorphic forms" and related terms herein refer to crystal forms of a molecule. Different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

The term "alkyl," as used herein refers to monovalent saturated aliphatic hydrocarbon groups, particularly, having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyl" as defined below.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl."

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octacene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

The term "subject" is defined herein to include animals such as mammals, including, but not limited to, primates (e.g., humans, monkeys, apes), cows, sheep, goats, horses, dogs, cats, rabbits, rats, mice and the like. In preferred embodiments, the subject is a human.

As used herein, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Thus, in one aspect, this invention relates to a method of treating cancer comprising administering to a patient in need thereof a therapeutically effective amount of a radiolabeled ether or alkyl phospholipid compound of Formula I

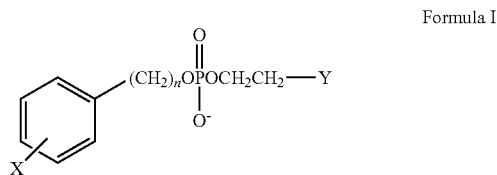

Formula I where X is an isotope of iodine; n is an integer between 12 and 30; and Y is selected from the group comprising $N^+H_3$, $HN^+(R)_2$, $N^+H_2R$, and $N^+(R)_3$, wherein R is an alkyl or arylalkyl substituent, or Formula II

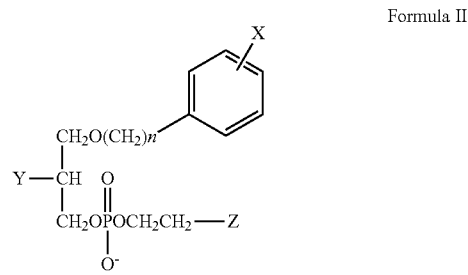

Formula II where X is an isotope of iodine; n is an integer between 12 and 30; Y is selected from the group consisting of H, OH, COOH, COOR and OR, and Z is selected from the group comprising $N^+H_3$, $HN^+(R)_2$, $N^+H_2R$, and $N^+(R)_3$, wherein R is an alkyl or arylalkyl substituent, wherein said therapeutically effective amount of said radiolabeled ether or alkyl phospholipid compound is sufficient to penetrate into said cancer stem cells and wherein a population of said cancer stem cells is reduced.

The therapeutically effective amount that is sufficient to penetrate into said cancer stem cells is preferably between 0.21-21 mg (equivalent to a 7-700 mCi, total mass dose range) and between 0.03-0.21 mg/kg (equivalent to 1-7 mCi/kg, by weight dose range).

These amounts were calculated using the current drug product (CLR1401) total mass dose value of 0.15 mg/mL and an activity concentration value of 5.0 mCi/mL at injection.

In one embodiment, the invention provides pharmaceutical compositions comprising radiolabeled ether or alkyl phospholipid compounds as described in the application formulated for use in the treatment of cancer wherein the radiolabeled ether or alkyl phospholipid compounds penetrate cancer stem cells.

In a preferred embodiment, the population of cancer stem cells comprises stem cells of the following cancers: glioma, lung cancer, squamous cell carcinoma, renal cancer, melanoma, colorectal cancer, ovarian cancer, prostate cancer, breast cancer, and pancreatic cancer.

For a therapy in humans, a preferred isotope of iodine is $^{131}I$, although other radioactive isotopes, including $^{123}I$, $^{124}I$, and $^{125}I$ can be used, too. In one embodiment, an ether or alkyl phospholipid compound tagged with "cold" iodine (e.g., $^{127}I$) can be utilized to treat cancer stem cells.

In the most preferred embodiment, the radiolabeled compound is CLR1404 (18-(p-iodophenyl)octadecyl phosphocholine) radiolabeled with $^{131}$I.

In addition, ether and alkyl phospholipid compounds having more than one radioactive iodine may be used for the purposes of the present invention. Some representative structures are as follows:

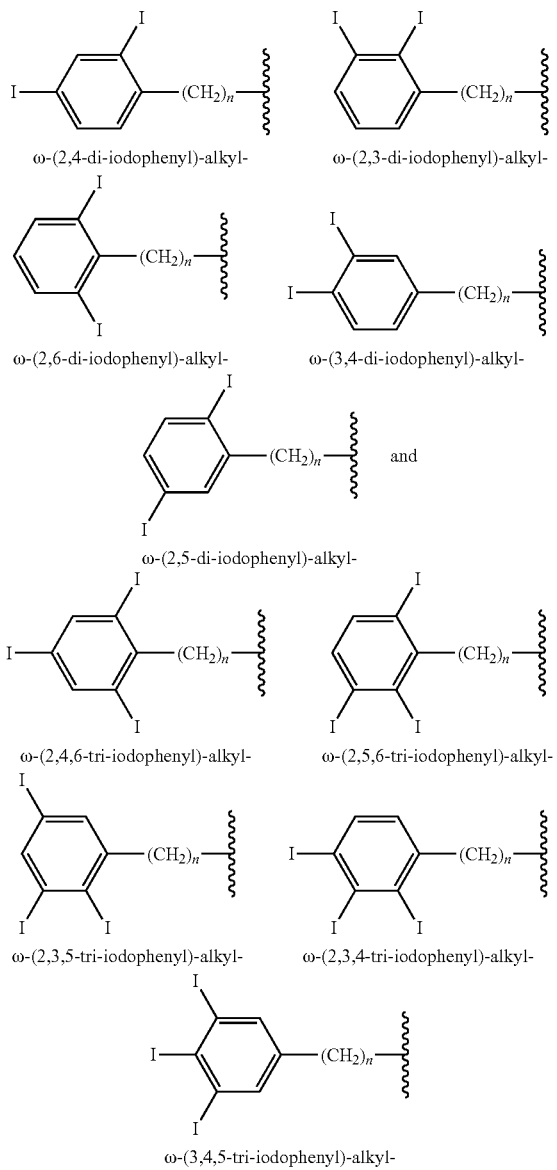

The part of the molecule after the vertical wavy line is the same as in the molecules with one Iodine attached to the phenyl ring.

In another embodiment, the invention also relates to a combination therapy, wherein the reduction of cancer stem cells with radiolabeled ether or alkyl phospholipid compounds takes place concurrently, subsequently, or prior to another treatment.

In a preferred embodiment, the other treatment is selected from radiotherapy, chemotherapy, tumor resection, ablative therapies, and local physical treatment on the basis of cold (cryo), heat (thermal), radiofrequency, and microwave.

In some embodiments of the invention, the claimed methods enhance the radiosensitivity of cancer stem cells. This is because PLE compounds, as described in the application, are able to penetrate cancer stem cells through direct uptake. Thus, the invention allows enhancing the overall radiation dose delivered to cancer stem cells by radiotherapy. In one embodiment, the invention allows enhancing the overall radiation dose delivered to cancer stem cells by radiotherapy by about 30%.

In another embodiment, the claimed methods may allow killing (or reducing the population of) cancer stem cells without any external radiation or any other cancer therapy. The killing of cancer stem cells by the described PLE analogs may be due to direct uptake of the PLE analogs into cancer stem cells and/or due to collateral effects from killing neighboring cancer cells.

In another embodiment, the invention relates to a method of imaging a population of cancer stem cells in vivo comprising administering to a patient in need thereof an effective amount of a radiolabeled alkyl phospholipid compound of Formula I

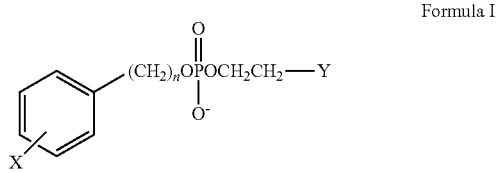

Formula I where X is an isotope of iodine; n is an integer between 12 and 30; and Y is selected from the group comprising $N^+H_3$, $HN^+(R)_2$, $N^+H_2R$, and $N^+(R)_3$, wherein R is an alkyl or arylalkyl substituent,
or Formula II

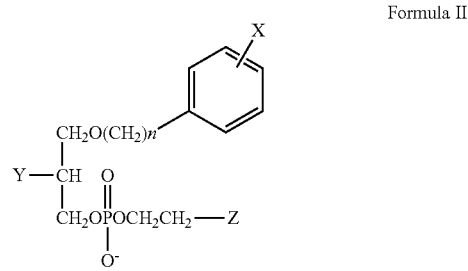

Formula II where X is an isotope of iodine; n is an integer between 12 and 30; Y is selected from the group consisting of H, OH, COOH, COOR and OR, and Z is selected from the group comprising $N^+H_3$, $HN^+(R)_2$, $N^+H_2R$, and $N^+(R)_3$, wherein R is an alkyl or arylalkyl substituent, wherein said radiolabeled ether or alkyl phospholipid compound penetrates said cancer stem cells.

In a preferred embodiment, the population of cancer stem cells comprises stem cells of the following cancers: glioma, lung cancer, squamous cell carcinoma, renal cancer, melanoma, colorectal cancer, ovarian cancer, prostate cancer, breast cancer, and pancreatic cancer.

For imaging in humans, a preferred isotope of iodine is $^{124}$I, although other radioactive isotopes, including $^{123}$I and $^{131}$I can also be used.

In the most preferred embodiment, the radiolabeled compound is CLR1404 (18-(p-iodophenyl)octadecyl phosphocholine) radiolabeled with $^{124}$I.

PLE compounds having more than one iodine atom attached to the phenyl ring, as described above, may also be used in the imaging methods.

In other embodiments of the invention, fluorescent analogs of PLE compounds may be used in the claimed imaging methods. For example, the invention specifically contemplates the use of CLR1501 compound, which has the following structure:

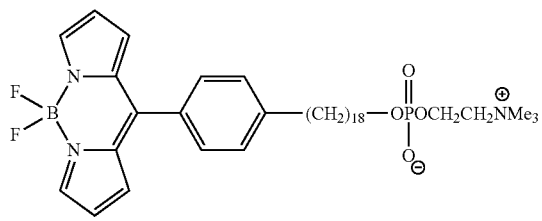

The application specifically incorporates by reference all fluorescent PLE analogs described in the pending patent application Ser. Nos. 12/463,970; 12/463,978; 12/463,983; 12/463,990; and 12/463,998.

The imaging can be performed through a hybrid scanning, utilizing a functional imaging modality, such as single photon emission computed tomography (SPECT) or positron emission tomography (PET) in combination with computed tomography (CT) and/or magnetic resonance imaging (MRI) techniques, and combinations thereof.

In another embodiment, the invention relates to a method of ex vivo or in vitro labeling cancer stem cells comprising administering to cells suspected of comprising cancer stem cells an effective amount of a radiolabeled ether or alkyl phospholipid compound of Formula I

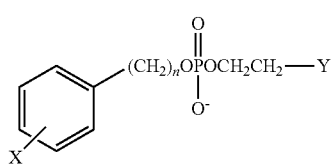

Formula I where X is an isotope of iodine; n is an integer between 12 and 30; and Y is selected from the group comprising $N^+H_3$, $HN^+(R)_2$, $N^+H_2R$, and $N^+(R)_3$, wherein R is an alkyl or arylalkyl substituent,
or Formula II

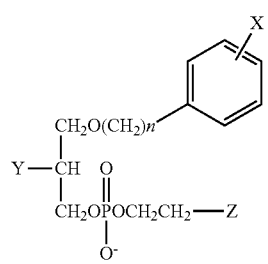

Formula II where X is an isotope of iodine; n is an integer between 12 and 30; Y is selected from the group consisting of H, OH, COOH, COOR and OR, and Z is selected from the group comprising $N^+H_3$, $HN^+(R)_2$, $N^+H_2R$, and $N^+(R)_3$, wherein R is an alkyl or arylalkyl substituent, wherein said cancer stem cells are labeled with said radiolabeled ether or alkyl phospholipid compound.

PLE compounds having more than one iodine atom attached to the phenyl ring, as described above, may also be used in the labeling methods.

In other embodiments of the invention, the above-described fluorescent analogs of PLE compounds may be used in the labeling methods.

In some embodiments, this method allows to detect and/or separate cancer stem cells from other types of cells.

In other embodiments, the described compounds can be used for identifying cancer stem cells in vivo, by administering the compounds to an animal and then identifying and/or quantifying stem cells of any type in any organ or tissue. These methods may be used to facilitate diagnosis and/or treatment of diseases or to study physiological processes in animals.

The compounds may be administered through any suitable method, including injection, ingestion, and topical administration.

The described methods may further comprise a step of separating the cancer stem cells from non-cancer cells.

In addition, these methods may be used to monitor the response to therapies which affect the growth of stem cells in animals, including humans. The therapies may either reduce the growth of stem cells or stimulate the growth of stem cells.

The following prophetic Examples demonstrate some aspects of the invention. The Examples are not meant to limit the invention in any way.

EXAMPLES

Example 1

Testing CLR1501 In Vitro to Determine if the Compound Enters Cancer Stem Cells

An objective of this experiment is to determine whether an alkyl phospholipid compound CLR1501 (a fluorescent version of CLR1404) enters cancer stem cells in culture utilizing confocal microscopy.

CLR1501 has the following structure:

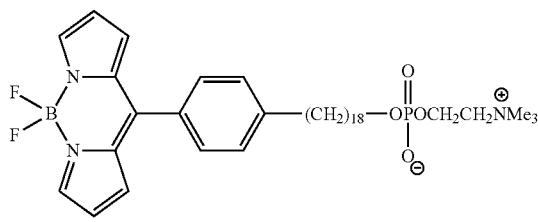

We have shown in cell culture studies that CLR1501 is preferentially taken up by a variety of tumor cells relative to their normal host tissue cells. The agent initially associates with outer cell membranes, becomes internalized, and then associates with other subcellular organelles and membranes. It does not appear to enter the nucleus even after 24 hours.

A similar experiment utilizing CLR1501 could be performed to demonstrate that alkyl phospholipid compounds can penetrate cancer stem cells. A comparison in brain tumors, for example, would consist of doing a parallel comparison of CLR1501 uptake in cultured glial cells (normal brain neuronal cells), normally differentiated glioma tumor cells, and enriched glioma cancer (isolated from human gliomas, separated using cancer stem cell markers, and grown in culture) stem cells. Following exposure to CLR1501, cells from each cohort would be removed from their cultured environments and subjected to z-stack confocal microscopy imaging over time and the uptake of the agent quantified to identify differences in total uptake and rates of uptake as well as retention.

A similar experiment can be done with radiolabeled CLR1404 with determination of the amount of compound that is retained in lysates of exposed stem cells.

Example 2

Testing CLR1404 In Vivo to Determine if the Compound Enters Cancer Stem Cells

An objective of this experiment is to determine whether $^{124}$I-CLR1404 enters cancer stem cells in vivo utilizing microPET/CT/MRI scanning.

Utilizing microPET/CT hybrid scanning of our tumor-bearing mouse models, we can quantitatively monitor tumor uptake and retention three-dimensionally in intact rodent tumor models, including xenografts of human tumors in immune-compromised mice, as well as spontaneous mouse and rat tumor models.

To evaluate the potential uptake of CLR1404 into cancer stem cells, using glioma as an example, we would perform in vivo microPET/CT/MRI hybrid scanning of anesthetized animals bearing orthotopic brain tumors derived from human glioma stem cells. Isolation of these cells would be similar to that described in Example 1, with the exception that the tumor stem cells would be implanted orthotopically into the mouse brain. A comparison would also be done with normal gliomas of non-stem cell derivation. Following in vivo imaging utilizing $^{124}$I-CLR1404 at several time points from 0-7 days, the tumors would be excised and scanned ex vivo and then the tumor isolated and counted for radioactivity in order to compare tumor to normal brain ratios and also to compare tumor derivations.

Example 3

Testing CLR1404 In Vivo to Determine if the Compound Reduces the Number of Cancer Stem Cells An objective of this experiment is to determine whether $^{125}$I- or $^{131}$I-CLR1404 can kill cancer stem cells and compare survival of normally differentiated glioma cells.

The same glioma model as proposed for the experiments in Examples 1 and 2 may be utilized. It would be desirable to compare the therapeutic efficacy of both $^{125}$I-CLR1404 and $^{131}$I-CLR1404. Accordingly, cohorts of brain tumor bearing mice would consist of sham operated (n=3), normally differentiated glioma (n=3), and stem cell derived glioma (n=6). Tumor would initially be confirmed noninvasively with high field MRI imaging prior to administration of the agent. Animals would receive a mixture of imaging ($^{124}$I) and therapeutic ($^{125}$I or $^{131}$I) agent at $T_0$ and scanned up to 4 days post injection to determine suitable tumor targeting. After a predetermined period of time, animals will be euthanized, tumors excised, cells digested and subjected to appropriate cell culture conditions. Cell growth of regularly differentiated glioma cells as well as gliomal stem cell derived spheroids will be quantified and compared to determine if there is differential killing effect for either isotope in each cell population.

The invention claimed is:

1. A method of treating cancer comprising administering to a patient in need thereof a therapeutically effective amount of 18-(p-iodophenyl)octadecyl phosphocholine) radiolabeled with $^{131}$I or $^{125}$I, wherein the cancer comprises cancer stem cells and the number of cancer stem cells is reduced, wherein the cancer is selected from the group consisting of glioma, lung cancer, squamous cell carcinoma, renal cancer, melanoma, colorectal cancer, ovarian cancer, prostate cancer, breast cancer, and pancreatic cancer, or any combination thereof.

2. The method of claim 1, wherein the isotope of iodine is $^{131}$I.

3. The method of claim 1, wherein the isotope of iodine is $^{125}$I.

4. The method of claim 1, wherein the method further comprises another cancer therapy selected from the group consisting of chemotherapy, tumor resection, ablative therapy, and local physical treatment on the basis of cold (cryo), heat (thermal), radiofrequency, and microwave.

* * * * *